United States Patent [19]

Gur et al.

[11] Patent Number: 4,535,780
[45] Date of Patent: Aug. 20, 1985

[54] APPARATUS FOR MEASURING XENON CONCENTRATION IN XENON CEREBRAL BLOOD-FLOW STUDIES

[75] Inventors: David Gur; John M. Herron, both of Pittsburgh, Pa.; Robert H. Pedersen, Milwaukee, Wis.

[73] Assignee: General Electric Company, Milwaukee, Wis.

[21] Appl. No.: 669,136

[22] Filed: Nov. 7, 1984

[51] Int. Cl.³ ............................................... A61B 6/00
[52] U.S. Cl. .................................... 128/659; 128/719; 128/716; 128/730
[58] Field of Search ................. 128/659, 719, 716, 730

[56] References Cited

U.S. PATENT DOCUMENTS 3,913,379 10/1975 Rusz et al. .......................... 128/719

FOREIGN PATENT DOCUMENTS 2322399 11/1973 Fed. Rep. of Germany ...... 128/716
2333572 1/1975 Fed. Rep. of Germany ...... 128/716

OTHER PUBLICATIONS

Seylaz et al., "Analytical Problems Associated with the Noninvasive Measurements of Cerebral Blood Flow in Cerebrovascular Diseases", Medical & Biological Eng. & Computing, Jan. 1980, pp. 39–47.

*Primary Examiner*—D. E. Gantz
*Assistant Examiner*—Chung K. Pak
*Attorney, Agent, or Firm*—Alexander M. Gerasimow; Douglas E. Stoner

[57] ABSTRACT

Apparatus for measuring xenon concentration in xenon cerebral blood-flow studies operates under the control of a microprocessor which is used to monitor the patient's breathing cycle and to control a sampling pump in order to assure that only end-tidal gas is sampled. A xenon gas mixture is delivered to a patient by means of a mask assembly. At the end of each exhale cycle, the patient's end-tidal gas is held in a chamber on the exhale side of the mask assembly. At the start of the next inhale cycle, the microprocessor activates the sampling pump which draws end-tidal gas into a thermal conductivity detector. The output of the detector is transmitted through an A/D converter and the resultant value stored in the microprocessor memory along with the time of the sample. At the completion of a CT scan series, the accumulated data in the microprocessor is transferred to the CT-system-housed computer to be used in the reconstruction of cerebral blood-flow images using conventional techniques.

11 Claims, 3 Drawing Figures

APPARATUS FOR MEASURING XENON CONCENTRATION IN XENON CEREBRAL BLOOD-FLOW STUDIES

BACKGROUND OF THE INVENTION

This invention relates to xenon-enhanced computerized tomography (CT). More particularly, this invention relates to apparatus for measuring xenon gas concentrations useful in derivation of cerebral blood-flow (CBF) estimates by xenon-enhanced computerized tomography.

A technique has been developed in recent years whereby images mapping the level and efficiency of cerebral blood flow can be generated on a CT scanner. The technique involves the inhalation of a xenon gas mixture by a patient during a series of CT scans. The xenon gas is absorbed into the patient's bloodstream and diffuses into surrounding tissue altering the X-ray absorption factor of the blood and diffused tissue. This change enhances the affected areas on the normal CT images. Over a series of scans, the rate of change in a region of tissue is a direct indication of the blood flow and diffusion rate in that region. Using data obtained over a series of scans it is possible to reconstruct, using known techniques, a blood-flow image where gray scale is proportional to blood-flow rate. These images are used to diagnose stroke cases and to screen potential stroke victims, as well as many other diagnostic procedures still in developmental stages.

The image reconstruction process requires that the concentration of xenon in the bloodstream be known at the time of each CT scan in the series. While various methods have been developed for measuring xenon concentration, all non-invasive methods derive bloodstream concentration by measuring the patient's end-tidal concentration in expired air. Xenon concentrations in end-expired gas are known emperically to be equivalent to xenon concentrations in arterial blood.

Most commonly, measurements of end-tidal xenon concentrations have been made by one of three basic methods. The subtraction method is based on the assumption that in a denitrogenated subject the exhaled gases are predominantly oxygen, carbon dioxide, water vapor and xenon, and that, therefore, the concentration of xenon can be obtained by subtracting the other three components from atmospheric pressure. This technique is acceptable provided oxygen and carbon dioxide concentrations can be measured with instruments having the requisite sensitivity and response speed. However, due to the fact that the subtraction method assesses xenon concentration in expired gas indirectly, it fails in patients who have not been completely denitrogenated. In addition, because the effects of pure oxygen inhalation on blood flow during denitrogination, it is preferable to perform blood-flow studies without that process. The end-tidal xenon concentration can be measured directly utilizing either a pre-calibrated mass spectrometer or a thermal conductivity detector. The mass spectrometer is the most accepted method for measuring xenon concentrations. However, the mass spectrometer is an expensive and complex device to operate. Conventional thermal conductivity detectors have been used successfully to measure xenon concentrations. In this type of system, the detector monitors the concentration of xenon in expired gas continuously. This system, used conventionally, provides the required accuracy but is limited by the relatively slow response time of the detector. At breath rates over approximately 18/minute or concentrations of over 40 percent, the detector cannot track the xenon concentration waveform accurately.

It is, therefore, an object of the invention to provide a low-cost, efficient and simple technique for measuring xenon concentrations in xenon CBF studies.

It is another object of the invention to provide an apparatus using a thermal conductivity detector for measuring xenon concentration in CBF studies which is independent of breath rate and xenon concentration.

It is still another object of the invention to provide an apparatus using a thermal conductivity detector for measuring xenon concentration in CBF studies wherein the detector responds substantially only to actual change in concentration from breath to breath.

SUMMARY OF THE INVENTION

In accordance with the invention, an apparatus is provided for measuring end-tidal xenon concentration in samples of air exhaled by a patient breathing a xenon-gas-containing mixture. The xenon concentration measurements are useful in combination with CT X-ray attenuation measurements of the region being studied to reconstruct images containing cerebral blood-flow information. The inventive apparatus includes means for providing the patient with a breathing mixture containing a predetermined amount of xenon gas and additionally includes means for storing the end-tidal air exhaled by the patient. A microprocessor is utilized to sense the beginning of the inhalation portion of the breathing cycle and for activating a pump which is used to draw the stored sample of end-tidal air into a thermal conductivity gas detector which is capable of providing an output indicative of the concentration of xenon gas in the sampled air. In this manner, the thermal conductivity detector responds to changes in breath-to-breath end-tidal concentrations only, rather than the much larger changes which occur over the full breathing cycle.

BRIEF DESCRIPTION OF THE DRAWING FIGURES

The features of the invention believed to be novel are set forth with particularity in the appended claims. The invention itself, however, both as to its organization and method of operation, together with further objects and advantages thereof, may best be understood by reference to the following description taken in conjunction with the accompanying drawings in which:

DETAILED DESCRIPTION OF THE INVENTION

Figure 1:
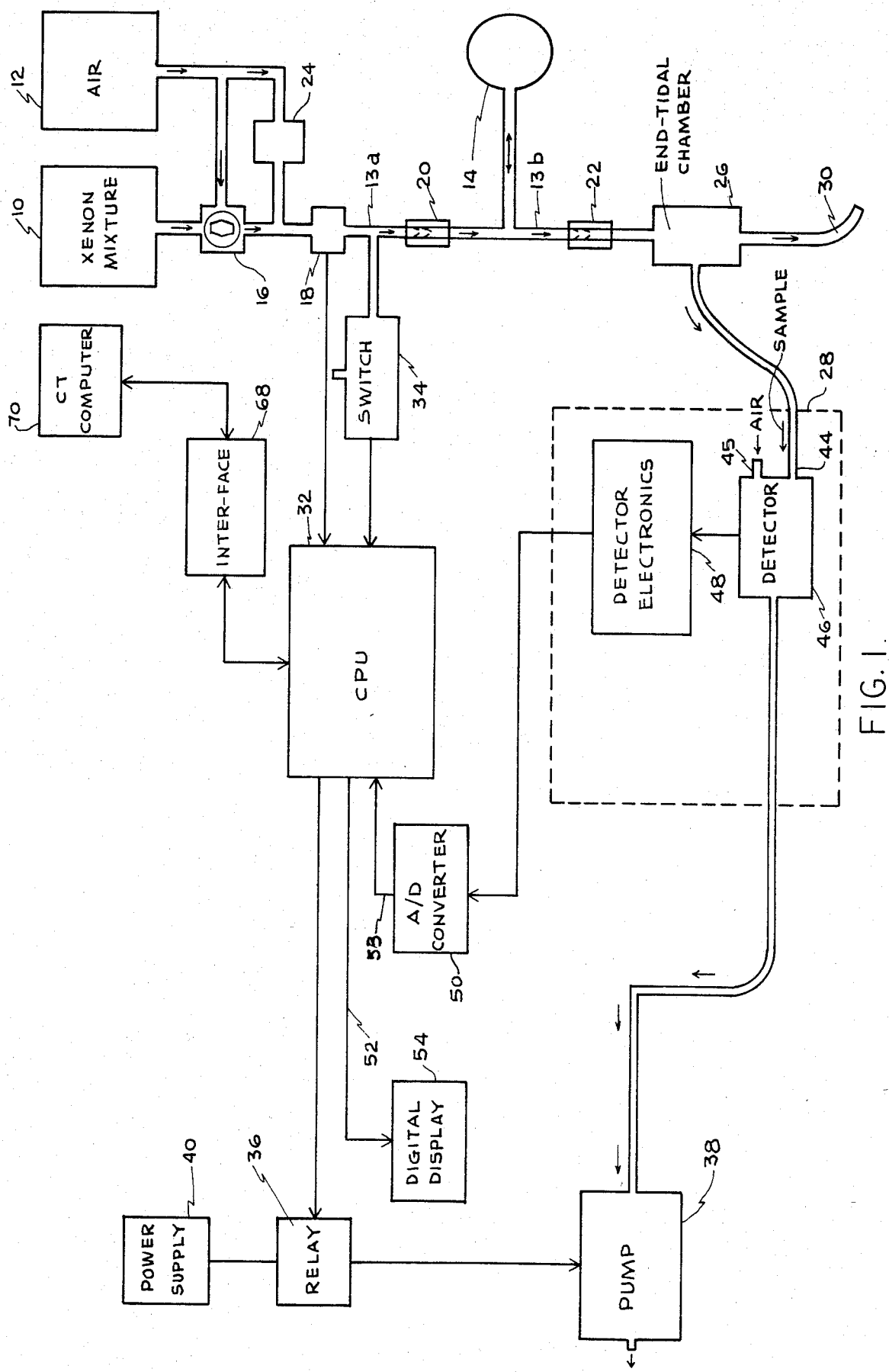
FIG. 1 is a system block diagram of an apparatus using a thermal conductivity detector for measuring xenon concentrations in accordance with the invention.

Referring first to FIG. 1, there is shown a system block diagram of the apparatus in accordance with the invention for the controlled sampling of expired air. The apparatus includes a reservoir 10 containing a breathing mixture of xenon gas and a second reservoir 12 containing either air or an oxygen-enriched atmosphere. The patient breathes, through a patient mask 14, a gas mixture selected from one of reservoirs 10 and 12, depending on the position of a source-selecting valve 16 which may conveniently comprise an electrically actuated solenoidal valve. Upon inhalation, the gas mixture from one of the reservoirs is drawn into the mask through an inhalation detector 18 and a one-way valve 20 connected in series along a length of tubing 13a. During the inhalation portion of the breathing cycle, a second one-way valve 22 connected in series along a length of exhaust tubing 13b is closed. An emergency by-pass valve 24 (e.g., magnetic or spring-loaded) provides an alternate path for air or oxygen from reservoir 12 to be supplied to the patient mask. During the exhalation portion of the breathing cycle, one-way valve 20 closes so that exhaled air is directed through one-way valve 22 to a reservoir, termed the end-tidal chamber 26. Excess exhaled air is vented through tubing 30 so that only the end-tidal air remains in the chamber. From chamber 26, the end-tidal air can be, in accordance with the invention, controllably drawn for thermal conductivity analysis into a gas detector, generally designated 28, which may comprise a modified unit, such as a Model 21-150 from Gow-Mac Instruments Corporation (Bridgewater, New Jersey).

System operation is under the control of a microprocessor-based central processing unit (CPU) 32 which may conveniently comprise a microcomputer board, such as the one bearing a standard designation SBC 80/28. The CPU is coupled to receive input signals from a pressure-activated switch 34, connected to sense pressure changes in tubing 13a. The pressure-activated switch is activated upon the occurrence of a pressure drop indicative of an emergency such as, for example, failure of check valve 18 to open at the beginning of the inhalation cycle as the patient draws air into the mask through one-way valve 20, while one-way valve 22 is closed. Check valve 18 is more sensitive than pressure switch 34 and in normal operation responds before switch 34 is activated. The check valve operates without any appreciable restriction of patient breathing and is used to detect the beginning of the inhalation cycle. In the preferred embodiment, the check valve includes a diaphragm (not shown) which deflects as the patient inhales. The deflection of the diaphragm interrupts an infrared beam. This interruption is sensed by an infrared detector (not shown) and is transmitted to the CPU as an indication of the beginning of the breathing cycle. It will, of course, be recognized that other methods for detecting the beginning of the inhalation cycle may be available and may be advantageously employed in practicing the invention. The significance in detecting the beginning of the inhalation cycle is that it indicates that the patient has just finished exhaling so that the exhaletidal chamber 26 has just received the end-tidal air. Therefore, since it is desirable to determine xenon concentrations in end-expired air, the output from check valve 18 is used to trigger the sampling process.

Sampling is initiated by CPU 32 providing an activating signal to a solid-state relay 36 which closes the circuit so that a sampling pump 38 is energized by a variable power supply 40. The sampling pump draws the end-tidal air held in chamber 26, at a fixed, but adjustable, rate, into an intake port 44 of a thermal conductivity detector 46 which forms part of detector unit 28. As described hereinbelow, detector 46 accommodates a pair of thermistors. The first thermistor senses the thermal conductivity of the end-tidal air, while the second thermistor measures the thermal conductivity of air, admitted through port 45, thereby providing a reference signal. The run-time and rate of pump 38 are selected to be sufficient to draw the sample into detector 46 for measurement. It will be recognized that if the pump is not properly adjusted the sample may be drawn through detector 46 preventing analysis of the sample (e.g., if the run-time and rate are too high). Of course, if the pump settings are too low the sample may not reach the detector. The correct settings depend on the particular system configuration. In one embodiment, it was found that a rate of 0.5 l/min. and a run time of 0.5 sec. were adequate.

A modification to the afore-identified model 21-150 detector, in accordance with the preferred embodiment, involves the disablement of a normally operating background flow pump. It has been found, in the particular application of the device to this invention, that in the presence of a continuous flow, the detector is less stable due to its sensitivity to flow rate. In accordance with the invention, measurements are performed in the absence of any substantial flow through the detector, thereby eliminating or minimizing flow variation as a factor. It should be recognized, however, that useful measurements have been performed with systems including an operational background flow pump.

Figure 2:
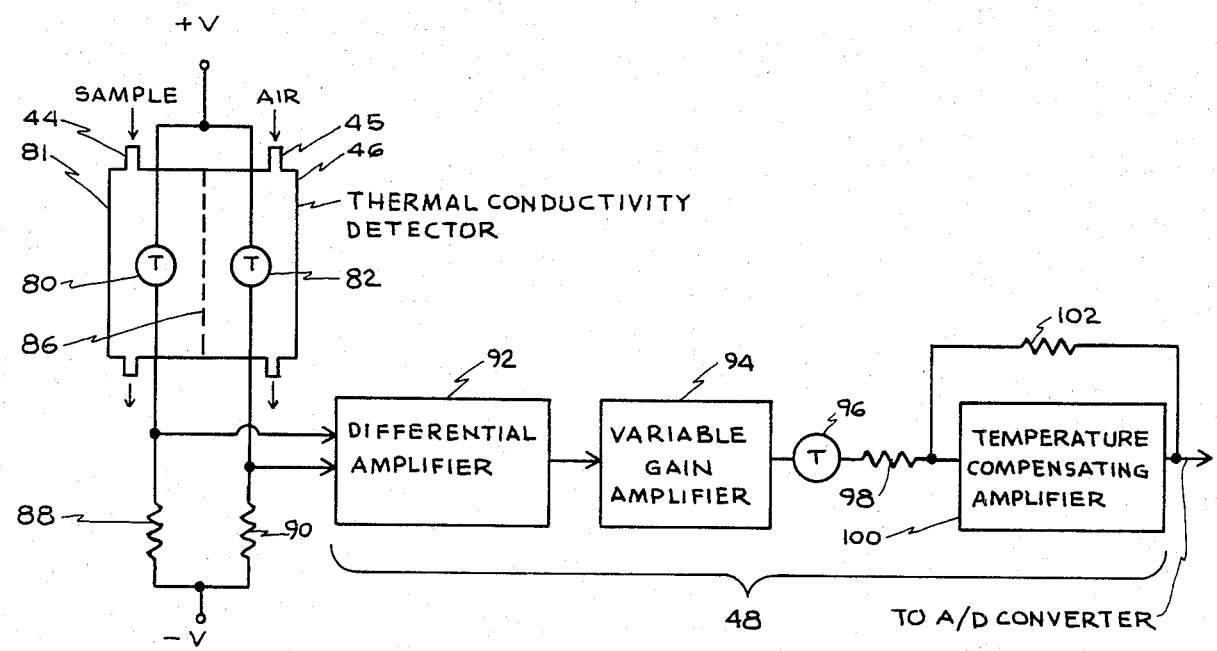
FIG. 2 depicts in block schematic form the thermal conductivity detector in accordance with one embodiment of the invention.

Further modifications to the Gow-Mac 21-150 unit will be described next with reference to FIG. 2. The changes relate principally to the detector 46 and calibration and gain electronics unit 48 shown in FIG. 1. Referring now to FIG. 2, the detector comprises two thermistors 80 and 82 located in a housing 81 and are thermally isolated from one another by a partition 86. Conveniently, a suitable thermal conductivity detector may be a Gow-Mac 10-133, wherein one of the thermistors (e.g., 80) samples the xenon gas flow, while another (e.g., 82) operates as a reference. Thermistors 80 and 82, along with resistors 88 and 90, are configured into a balanced bridge circuit which is connected to a differential amplifier 92 for detecting bridge imbalance. The differential output of amplifier 92 is applied to a variable gain amplifier 94 and thence through series-connected thermistor 96 and resistor 98 to temperature compensating amplifier 100. The output of amplifier 100 is applied to A/D converter 50. Since the gain of amplifier 100 is dependent upon the ratio of a feedback resistor 102 and the joint resistance of thermistor 96 and resistor 98, temperature compensation is achieved by changes in the resistance value of thermistor 96 which is strategically located on housing 81 of detector 46. In the preferred embodiment, amplifiers 92, 94, and 100 are implemented using conventional operational amplifier devices.

Continuing now with reference to FIG. 1, the output signals from amplifier 100 are digitized in an analog-to-digital (A/D) converter 50 and applied to CPU 32 by means of a bus 53. A digital display meter 54, coupled to CPU 32, is properly calibrated to display the percent of xenon concentration. A real-time clock is used by the CPU to record the time at which each sample is analyzed. This information is needed in order to correlate the xenon concentration data to the timing of the CT scan series during the image reconstruction process.

Actual system control is by means of an operator control console (not shown) which is part of a host computer 70 which comprises part of the CT scanning apparatus (not shown). Communication between the CPU and computer 70 is through a two-way RS232 to current loop converter 68. In use, the system progresses through three modes of operation. In the first mode, the system sequences through its internal initialization and diagnostic routines. Upon completion of the initialization and diagnostic routines, the system enters a standby condition while monitoring the CT computer for a command to begin the calibration phase.

The purpose of the calibration phase is to establish a zero-percent xenon concentration reference value. During this phase, the CPU monitors the patient's breathing cycle. At this point in the study, the patient breathes room air or oxygen from reservoir 12 through the mask assembly 14. The CPU samples the end-tidal mixture for four consecutive breaths and averages the measured results to determine a detector offset value and to define a zero-concentration reference. This value is transmitted through converter 68 to host computer 70. The transmission is accomplished at the completion of the study and is used to correct for any offset level in the actual xenon concentration data values. The offset value is also subtracted from the measured values during the monitoring phase to provide a corrected value for the percent xenon display meter 54.

After the offset value is computed and stored, CPU 32 stops sampling and begins monitoring for a command to enter the monitoring phase. It is during the monitoring phase that the actual xenon concentration data is collected and stored.

Upon entering the monitoring phase, CPU 32 once again begins monitoring the patient's breathing cycle in a manner described hereinbefore. In anticipation of entering the monitoring phase, mask source selector valve 16 is switched to provide breathing mixture from reservoir 10 containing a mixture of xenon and oxygen. At this time, the CT scanner also initiates the xenon CBF scan series, although scans are also performed prior to administering xenon to provide reference images. In the monitoring phase, at the start of each inhale portion of the breathing cycle, the end-tidal mixture from the previous breath is sampled and the xenon concentration measured and stored along with the time the sample was taken (real-time clock information) in a data table within the CPU's internal memory. One entry is made in the table for every patient breath while the system is in the monitoring mode, until completion of the study.

In the monitoring phase, the system will continue to monitor and record xenon concentrations until it is either instructed to discontinue sampling by the host computer via converter 68 (indicating that the CT scan cycle has been completed), or that the number of sample points has exceeded, in one embodiment, approximately 1500, at which point the data-table storage capacity in CPU 32 is depleted. It has been found that the storage capacity for 1500 sample points is adequate for normal operation.

At the completion of the CT scan series, host computer 70 is programmed to command CPU 32 through converter 68 to stop sampling and transfer the contents of the data table to the host computer. The computer then utilizes the xenon concentration data along with the X-ray attenuation data acquired during the CT scan to perform cerebral blood-flow image reconstruction using known techniques.

Figure 3:
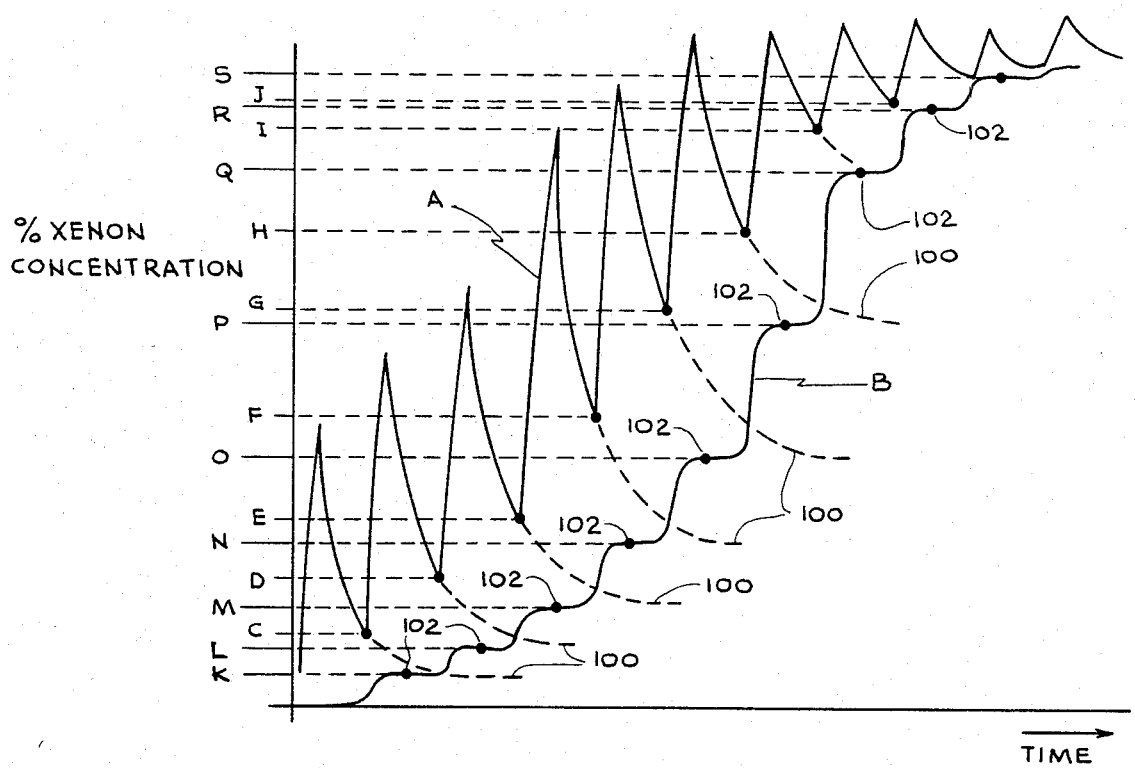
FIG. 3 compares graphically xenon concentrations in exhaled air measured conventionally and in accordance with the invention.
Figure 1:
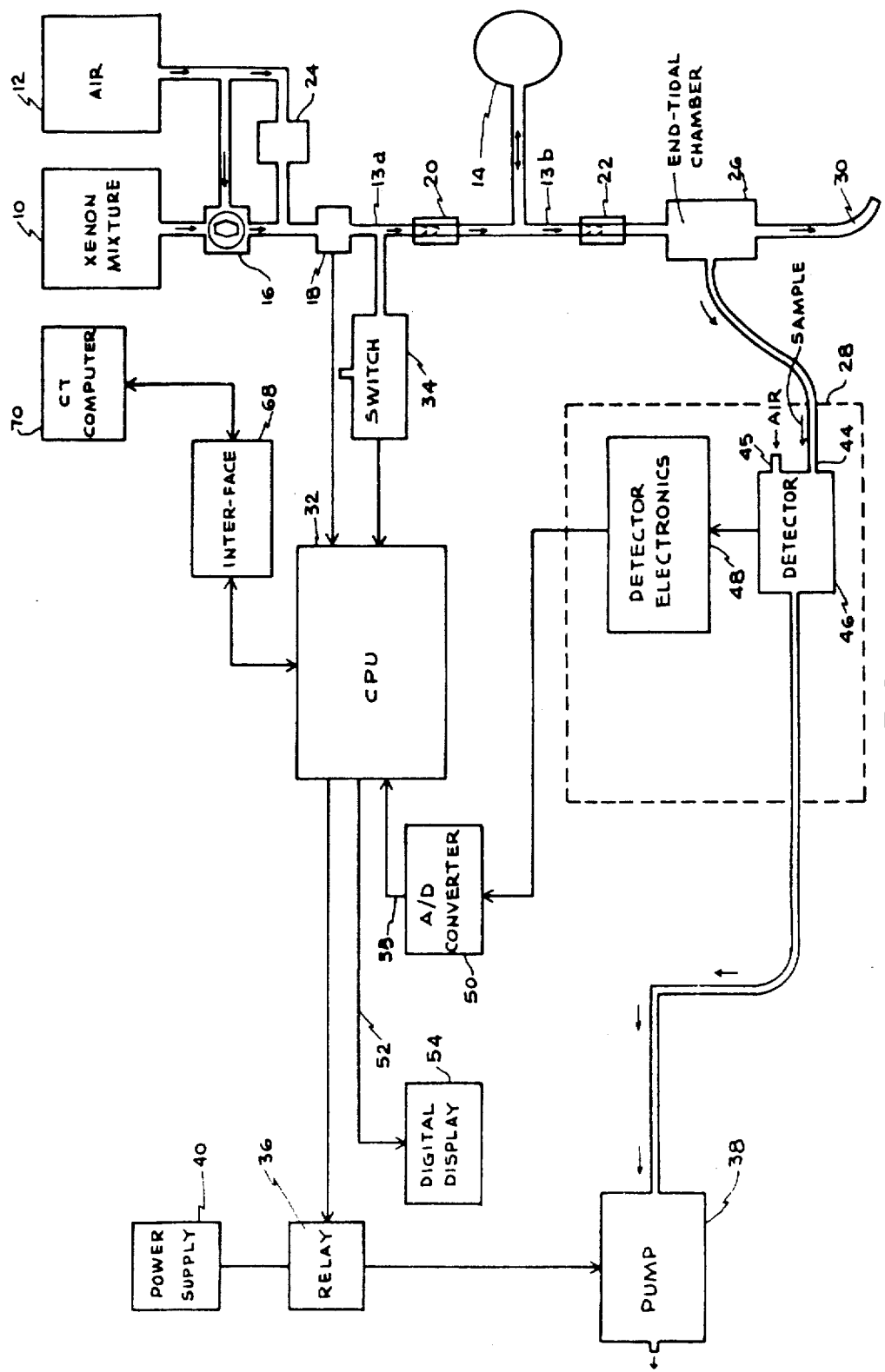

FIG. 3 depicts in graphical form the output, designated A, of a conventional (continously sampling thermal conductivity detector) and the output, designated B, of a thermal conductivity in accordance with the invention, as described hereinbefore. In FIG. 3, the percent of xenon concentration is indicated along the vertical axis, while time (corresponding to progressive breathing of a xenon mixture by the patient) is shown along the horizontal axis. For breathing rates exceeding apporximately 18 breaths/minute (situation depicted in FIG. 3), the conventional detector is not capable of following the large variations in xenon concentrations during the breathing cycle. In this case, referring to curve A, the measurements of xenon concentrations obtained will be C-J, indicated along the vertical axis. Values C-J, however, are not the correct xenon concentrations for end-tidal air. The desired values are K-S, associated with curve B, as suggested by the dash line extensions (collectively identified by reference numeral 100) of curve A, which eventually stabilize at same concentration values as points K-S. Xenon concentration values K-S are in fact those measured by the inventive thermal conductivity detector. Points identified by reference numeral 102 in curve B designate times when the CPU reads the output of the A/D converter. The more precise measurements are obtained due to the fact that the detector in accordance with the invention responds to changes in breath-to-breath end-tidal concentrations only, rather than the much larger changes which occur over the full breathing cycle.

From the foregoing, it will be recognized that there is provided in accordance with the invention a thermal conductivity detector capable of performing xenon concentration measurements economically, efficiently, and simply. The operation of the inventive detector is independent of breath rate and xenon concentrations, since the detector responds substantially only to actual changes in concentration from breath to breath.

While this invention has been described with reference to particular embodiments and examples, other modifications and variations will occur to those skilled in the art in view of the above teachings. Accordingly, it should be understood that within the scope of the appended claims the invention may be practiced otherwise than is specifically described.

The invention claimed is:

1. An apparatus for measuring end-tidal xenon concentration in samples of air exhaled by a patient breathing a xenon-gas-containing atmosphere, said xenon gas concentration measurement being useful in combination with CT X-ray attenuation measurements to reconstruct images containing cerebral blood-flow information, said apparatus comprising:
   means for retaining xenon-containing end-tidal air exhaled by the patient;
   means for sensing the beginning of the inhalation portions of successive breathing cycles, and providing signals indicative thereof;
   thermal conductivity gas-detector means capable of providing an output signal indicative of the concentration of xenon gas in a sample of the exhaled end-tidal air;
   pump means for drawing a sample of end-tidal air from said means for retaining; and
   control means responsive to each of said signals from said means for sensing to provide an activating signal to said pump means to draw a sample of end-tidal air held in said means for retaining into said thermal conductivity detector for analysis.

2. The apparatus of claim 1 wherein said thermal conductivity gas-detector means comprises a first thermistor means for performing measurements on said sample and a second thermistor means for providing a reference signal.

3. The apparatus of claim 2 wherein said thermal conductivity gas-detector means comprises calibration and gain-adjustment means for conditioning the output signal indicative of the concentration of xenon gas in said sample.

4. The apparatus of claim 3 further comprising a third thermistor means operatively coupled to said calibration and gain adjustment means for compensating for ambient temperature variations in the vicinity of said first and second thermistor devices.

5. The apparatus of claim 4 wherein said activating signal is applied to said pump means for a time sufficient to draw a sample of end-tidal air held in said means for retaining into said thermal conductivity gas detector, and is thereafter disabled such that analysis of said sample is performed substantially in the absence of air flow through said thermal conductivity gas detector.

6. The apparatus of claim 2 wherein said thermal conductivity gas-detector means comprises a third thermistor means for temperature compensating the output indicative of the concentration of xenon gas in said sample.

7. The apparatus of claim 1 wherein said thermal conductivity gas-detector means further comprises thermistor means for temperature compensating the output indicative of the concentration of xenon gas in said sample.

8. The apparatus of claim 1 wherein said thermal conductivity gas-detector means comprises calibration and gain-adjustment means for conditioning the output signal indicative of the concentration of xenon gas in said sample.

9. The apparatus of claim 8 further comprising thermistor means operatively coupled to said calibration and gain adjustment means for compensating for ambient temperature variations in the vicinity of said first and second thermistor devices.

10. The apparatus of claim 1 wherein said activating signal is applied to said pump means for a time sufficient to draw a sample of end-tidal air held in said means for retaining into said thermal conductivity gas detector, and is thereafter disabled such that analysis of said sample is performed substantially in the absence of air flow through said thermal conductivity gas detector.

11. The apparatus of claim 1 further comprising means for providing a patient with a breathing mixture containing xenon gas.

* * * * *

UNITED STATES PATENT AND TRADEMARK OFFICE
CERTIFICATE OF CORRECTION

PATENT NO. : 4,535,780

DATED : Aug. 20, 1985

INVENTOR(S) : David Gur, et al.

It is certified that error appears in the above-identified patent and that said Letters Patent is hereby corrected as shown below:

Column 6, line 6, "apporximately" should read
-- approximately --.

Add "Sheet 1 of 2" to show Fig. 1 as shown on the attached sheet.

Delete on of the "Sheet 2 of 2" in the patent.

Signed and Sealed this

Fourth Day of February 1986

[SEAL]

Attest:

DONALD J. QUIGG

*Attesting Officer*  *Commissioner of Patents and Trademarks*